United States Patent [19]
Taylor

[11] 4,242,274
[45] Dec. 30, 1980

[54] PROCESS FOR THE PREPARATION OF 2,2-DIPHENYL-4-(DIMETHYLAMINO)-PENTANE NITRILE

[75] Inventor: John J. Taylor, St. Peters, Mo.

[73] Assignee: Mallinckrodt, Inc., St. Louis, Mo.

[21] Appl. No.: 49,412

[22] Filed: Jun. 18, 1979

[51] Int. Cl.$^3$ .................... C07C 97/10; C07C 121/78
[52] U.S. Cl. .............................. 260/465 E; 564/319
[58] Field of Search ................ 260/465 E, 570 R

[56] References Cited
U.S. PATENT DOCUMENTS

| | | | |
|---|---|---|---|
| 3,992,432 | 11/1976 | Napier et al. | 260/465.1 |
| 4,056,509 | 11/1977 | Verbrugge et al. | 260/465 G |

OTHER PUBLICATIONS

Schultz et al., J. Amer. Chem. Soc., vol. 69, 188 and 2458 (1947).

Brändström et al., Tetrahedron Letters, No. 6, pp. 473-474 (1972).

*Primary Examiner*—Dolph H. Torrence
*Attorney, Agent, or Firm*—Senniger, Powers, Leavitt and Roedel

[57] ABSTRACT

A process for the preparation of 2,2-diphenyl-4-(dimethylamino)-pentane nitrile. A charge mixture is prepared comprising diphenylacetonitrile, 1-(dimethylamino)-2-halopropane, a base, water, a water-immiscible organic solvent, and a quaternary salt selected from a group consisting of tetrabutylammonium halides, tetrabutylammonium hydrogen sulfate, cetyltrimethylammonium halides, benzyltriphenylphosphonium halides, and methyltrialkyl ($C_8$–$C_{10}$) ammonium halides. The mixture is heated under an inert atmosphere to effect formation of 2,2-diphenyl-4-(dimethylamino)-pentane nitrile by reaction of diphenylacetonitrile, 1-(dimethylamino)-2-halopropane and a base.

8 Claims, 1 Drawing Figure

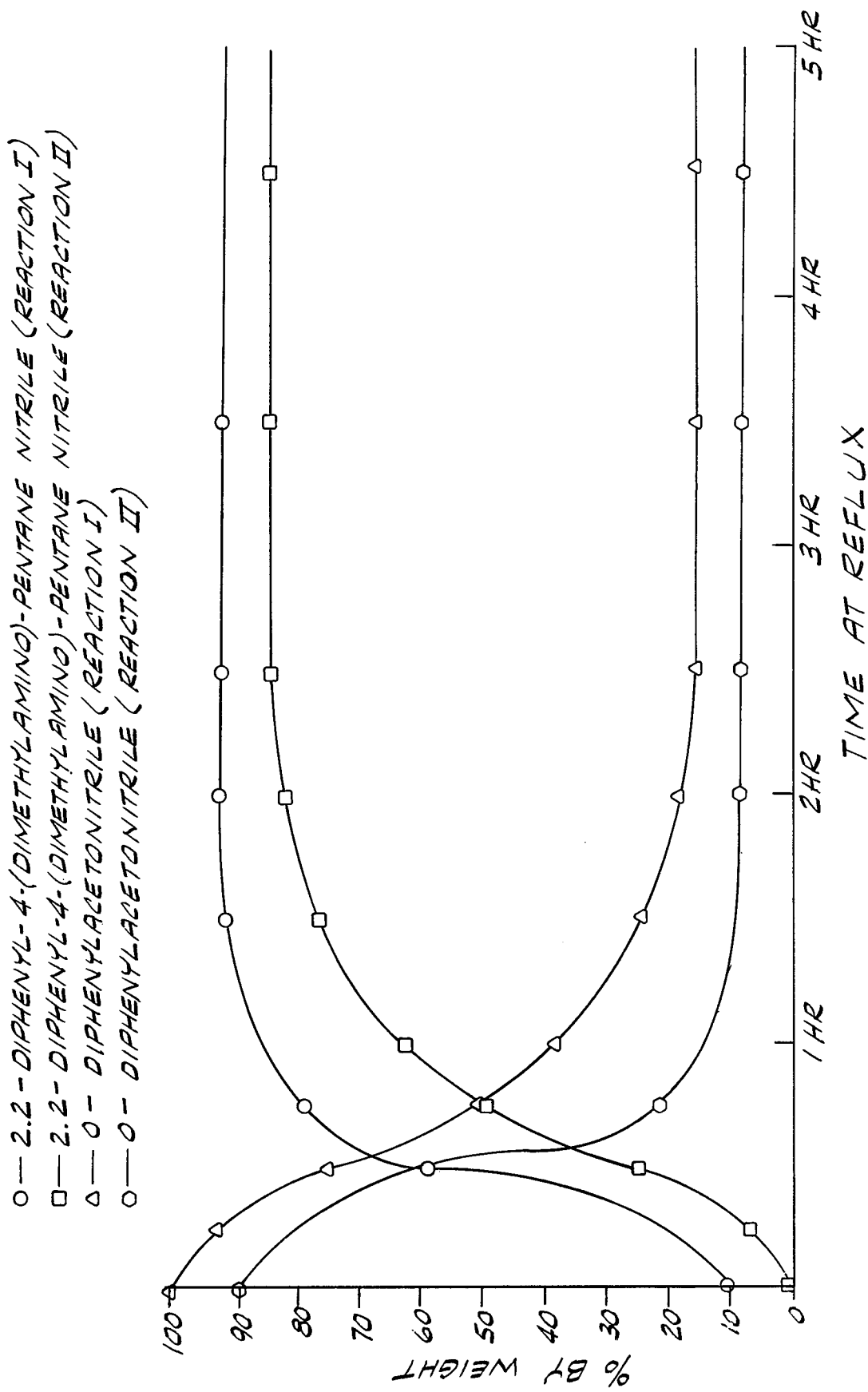

PROCESS FOR THE PREPARATION OF 2,2-DIPHENYL-4-(DIMETHYLAMINO)-PENTANE NITRILE

BACKGROUND OF THE INVENTION

This invention relates to the manufacture of methadone and more particularly to an improved process for preparing the methadone precursor 2,2-diphenyl-4-(dimethylamino)-pentane nitrile.

Methadone hydrochloride, i.e. 6-(dimethylamino)-4,4-diphenyl-3-heptanone hydrochloride is widely used as a narcotic analgesic, particularly in clinical treatment for withdrawal from heroin addiction. Methadone is prepared by reaction of 2,2-diphenyl-4-(dimethylamino)-pentane nitrile with an ethylmagnesium halide.

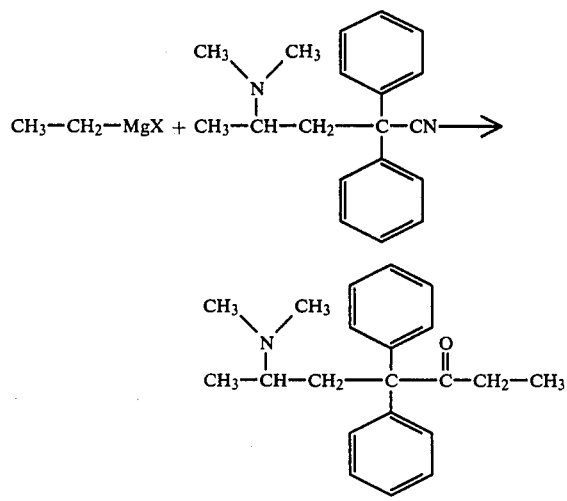

Conventionally the amino nitrile precursor is prepared by the reaction of diphenylacetonitrile with 1-(dimethylamino)-2-halopropane and base. See Schultz et al. Journal of the American Chemical Society, 69, 188 and 2458 (1947). In this reaction the base abstracts a proton from the diphenylacetonitrile and induces formation of a cyclic ethylenimmonium ion intermediate from the 1-(dimethylamino)-2-halopropane

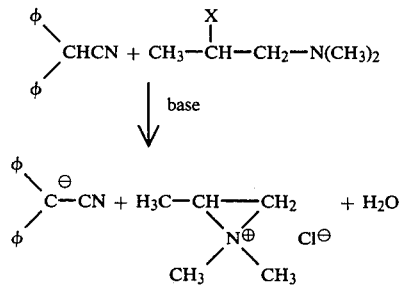

The carbanion can react at either of two sites on the ethylenimmonium ion to produce either the desired intermediate 2,2-diphenyl-4-(dimethylamino)-propane nitrile or its isomer 2,2-diphenyl-3-methyl-4-(dimethylamino)-butyronitrile.

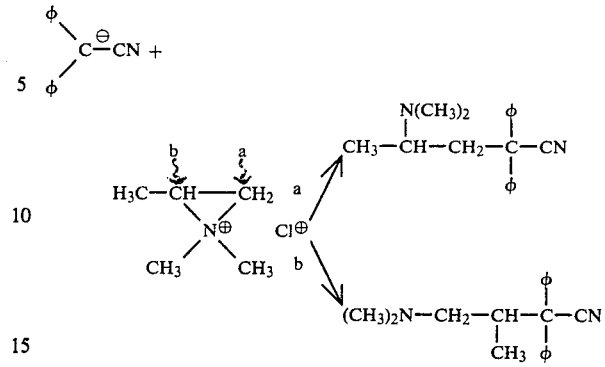

When the synthesis of the intermediate is carried out, approximately equal proportions of both the methadone precursor and its isomer are formed.

In order to drive the reaction of diphenylacetonitrile and 1-(dimethylamino)-2-halopropane substantially to completion, it is necessary to azeotropically remove water from the reaction zone. A lengthy reaction period is required to azeotrope off the water and obtain the desired conversion of approximately 85%. As a consequence, the productivity of the methadone manufacturing process is relatively low.

After completion of the above-described reaction, the methadone precursor must be isolated from its isomer and other components of the reaction mixture. This is conventionally accomplished by acidifying the reaction mixture with hydrochloric acid thereby forming the hydrochlorides of both amino nitrile isomers, which then concentrate in the aqueous phase. Thereafter, the phases are separated and an oil comprising the isomers is precipitated by addition of NaOH. Separation of the isomers is carried out by dissolving the oil in isopropyl alcohol and crystallizing 2,2-diphenyl-4-(dimethylamino)-pentane nitrile from the solution.

SUMMARY OF THE INVENTION

Among the several objects of the present invention may be noted the provision of an improved process for the manufacture of methadone and in particular an improved process for the synthesis of the 2,2-diphenyl-4-(dimethylamino)-pentane nitrile precursor; the provision of such a process which eliminates the need for azeotropic removal of the water by-product of the reaction; the provision of such a process which improves the productivity of the step of synthesizing the precursor; the provision of such a process which affords high yields of the precursor in a significantly shortened reaction cycle; and the provision of such a process which includes an improved method for recovery of the precursor.

Briefly, therefore, the present invention is directed to a process for the preparation of 2,2-diphenyl-4-(dimethylamino)-pentane nitrile. In this process, a charge mixture is prepared comprising diphenylacetonitrile, 1-(dimethylamino)-2-halopropane, a base, water, a water-immiscible organic solvent, and a quaternary salt selected from the group consisting of tetrabutylammonium halides, tetrabutylammonium hydrogen sulfate, cetyltrimethylammonium halides, benzyltriphenylphosphonium halides, and methyltrialkyl ($C_8$-$C_{10}$) ammonium halides. The charge mixture is heated under an inert atmosphere to effect formation of 2,2-diphenyl-4-

(dimethylamino)-pentane nitrile by reaction of diphenylacetonitrile, 1-(dimethylamino)-2-halopropane and base.

Other objects and features will be in part apparent and in part pointed out hereinafter.

BRIEF DESCRIPTION OF THE DRAWING

The single FIGURE of the drawing shows comparative reaction profiles for the reaction between diphenyl acetonitrile, sodium hydroxide and 1-dimethyl-3-halopropane, both uncatalyzed and as catalyzed with tetrabutylammonium bromide.

DESCRIPTION OF THE PREFERRED EMBODIMENTS

In accordance with the present invention, it has been discovered that substantially improved productivity is realized where the reaction of diphenylacetonitrile with 1-dimethylamino-2-halo-propane and base is carried out in the presence of a quaternary ammonium or phosphonium salt. The quaternary salt exercises a catalytic effect on the reaction, markedly increasing the reaction rate and thereby permitting the improved productivity to be realized. Obviated is the need for azeotropic removal of reaction by-product water to drive the reaction forward.

Advantageous yields are also provided by the process of the invention. Although the yields obtained are the same for the catalyzed and uncatalyzed processes where the reaction is carried fully to completion, for shortened reaction cycles of 2-4 hours which provide the highest productivity the process of the invention provides superior yields. The proportions of 2,2-diphenyl-4-(dimethylamino)-pentane nitrile produced relative to its isomer, 2,2 diphenyl-3-methyl-4-(dimethylamino)-butyronitrile, are the same as in the uncatalyzed process.

Certain particular catalysts have been found to have an especially advantageous effect in promoting the reaction between diphenylacetonitrile, base and 1-dimethylamino-2-halopropane. The most preferred catalysts include tetrabutylammonium chloride, tetrabutylammonium bromide, tetrabutylammonium iodide, and tetrabutylammonium hydrogen sulfate. Other effective catalysts include cetyltrimethylammonium chloride, cetyltrimethylammonium bromide, cetyltrimethylammonium iodide, benzyltriphenylphosphonium chloride, benzyltriphenylphosphonium bromide, benzyltriphenylphosphonium iodide, and the corresponding methyltrialkyl ($C_8$-$C_{10}$) ammonium halides.

To carry out the synthesis of the precursor, a reactor is charged with organic solvent, 1-dimethylamino-2-halopropane, diphenylacetonitrile, base, quaternary salt catalyst, and an aliquot of water.

Preferably the base is sodium hydroxide or potassium hydroxide. Alternatively, sodium carbonate, trisodium phosphate, potassium carbonate, tripotassium phosphate and similar highly alkaline alkali metal salts may be used. The t-butoxides and azides of sodium and potassium may also be utilized but are not preferred because of the explosion hazard that they present. Where either sodium or potassium hydroxide is utilized as the base, it is conveniently introduced into the charge as an aqueous solution, typically having a strength of 50% by weight.

Essentially any suitable water-immiscible organic solvent can be utilized for the reaction. Aromatic solvents are preferred, however, and toluene and xylene are most preferred. Toluene is a highly suitable solvent because the reaction proceeds rapidly and satisfactorily at toluene atmospheric reflux temperature. The use of a xylene solvent permits even higher reaction temperatures under atmospheric reflux conditions. Benzene is an effective solvent for the reaction but is not preferred both because of its toxic properties and also because of the need to maintain the reaction under pressure to achieve the desired reaction temperatures.

Although the reactant ratios are not highly critical it is preferred to charge a moderate excess of 1-dimethylamino-2-halopropane so as to maximize the conversion of diphenylacetonitrile. An excess of base is also preferably charged.

Substantial improvement in reaction rate as compared to the uncatalyzed process is achieved if the concentration of the quaternary salt catalyst is at least about 7 mole percent based on the diphenylacetonitrile concentration. Preferably at least about 10% of the catalyst is used. Higher concentrations of catalyst can be employed but are generally unnecessary.

In order to inhibit the oxidation of diphenylacetonitrile and the formation of by-product benzoquinone, the reaction is preferably carried out under an inert atmosphere, for example, under a nitrogen blanket. As noted, it is convenient to conduct the reaction at toluene reflux temperature. This may typically be in the range of between about 88° and about 95° C. Xylene reflux permits higher reaction temperatures. As a general proposition, the reaction should be carried out at a temperature of at least about 80° C. Where the reaction is carried out at toluene reflux and with catalyst concentration of 10 mole percent based on diphenylacetonitrile, an 85–99% conversion to total amino nitriles is obtained, with a 40–45% conversion to the desired isomer, 2,2-diphenyl-4-(dimethylamino)-pentane nitrile.

The exact mechanism by which the quaternary salt acts as a catalyst in accelerating the reaction rate is not known. Quaternary ammonium and phosphonium salts are known to be so called "phase transfer" catalysts which promote certain reactions by conveying reactants or intermediates into the phase in which reaction occurs. According to the literature, it is generally believed that anionic or nucleophilic intermediate species formed in the aqueous phase combine with the quaternary ammonium or phosphonium cation to provide an intermediate whose distribution between phases favors the organic phase to a significantly greater extent than does the distribution of the nucleophile itself. It is further thought that the combined species reacts in the organic phase with another organic-soluble reactant, e.g., an alkyl halide, to produce the desired product, thereby regenerating the quaternary salt which returns to the aqueous phase and is available for further combination with the nucleophile.

Although this mechanism may be at work in the reactions of the invention, it does not appear to explain either the need for water removal during the uncatalyzed reaction nor the specific effect of the quaternary salt in eliminating this need. Despite the fact that I am thus unable to provide a definitive explanation of the mechanism involved, I have nonetheless found that certain quaternary salt catalysts have a highly advantageous effect on the rate, productivity and yield of the precursor formation reaction where the conditions outlined above are maintained.

In the process of the invention, a further improvement over the conventional method is provided in the steps for recovery of 2,2-diphenyl-4-(dimethylamino)-pentane nitrile from the reaction mixture. In accordance with the improved method, the basic aqueous phase containing catalyst, reaction salts and excess base, is separated from the organic phase. The organic phase is then washed with water for removal of residual water-soluble impurities. After the washing step is complete, the solvent is stripped off, preferably under vacuum, to leave an oil which comprises the methadone precursor, its isomer 2,2-diphenyl-3-methyl-4-(dimethylamino)-butyronitrile, and any unreacted diphenylacetonitrile or 1-dimethylamino-2-halopropane. To separate the isomers and isolate the methadone precursor, the oil is dissolved in a suitable solvent such as isopropyl alcohol and the resultant solution is cooled, thereby effecting crystallization of the desired precursor material.

Methadone is prepared by the Grignard reaction between 2,2-diphenyl-4-(dimethylamino)-pentane nitrile and an ethylmagnesium halide such as ethylmagnesium bromide.

The following examples illustrate the invention.

EXAMPLE 1

To a reaction flask containing toluene (125 ml) was charged 1-dimethylamino-2-chloropropane hydrochloride (50 g), diphenylacetonitrile (50 g), a 50% aqueous solution of sodium hydroxide (80 g), water (40 ml), and a methyltrialkyl ($C_8$-$C_{10}$) ammonium chloride sold under the trade designation Adogen 464 by Ashland Chemical (4 g). The charge mixture was heated to reflux under a nitrogen atmosphere and stirred at reflux temperature for two hours. Heat was then withdrawn and the reaction mixture allowed to cool for about 30 min.

After cooling the reaction mixture was transferred to a separatory funnel where it was mixed with distilled water (approximately 200 ml) and thereafter allowed to separate (2-3 min). After the phases had separated, the bottom water layer, which had a pH of approximately 13, was drawn off. The organic phase (approximately 220 ml) was then transferred to a beaker and additional water (100 ml) was added. The contents of the beaker were stirred and hydrochloric acid was added until the pH of the water phase was reduced to 2-3. This required approximately 25 ml of acid. Addition of acid formed the hydrochloride salt of 2,2 diphenyl-4-(dimethylamino)-pentane nitrile and 2,2-diphenyl-3-methyl-4-(dimethylamino)-butyronitrile which thereupon were extracted into the water phase. After the extraction was complete the phases were separated, providing an aqueous product layer (approximately 220 ml) and an extracted organic layer (approximately 130 ml). Thereafter another aliquot of water (50 ml) was added to the extracted organic layer and the pH of the water phase again adjusted to 2-3. The aqueous phase was separated and combined with the aqueous phase from the initial stage of the extraction to provide an aqueous product phase having a total volume of approximately 280 ml. The spent organic phase (approximately 120 ml) containing unreacted organic starting materials was discarded.

To the aqueous product phase, a 50% sodium hydroxide solution was added with stirring until the pH was increased to approximately 13. This required approximately 40 ml of caustic solution. Addition of caustic converted the hydrochloride salts to the free amines which commenced to separate from the organic phase. The mixture was heated to 60°-65° C. to promote separation, and transferred to a separatory funnel where the bottom aqueous phase was separated and discarded. Adequate separation required approximately 30 min. The oil layer remaining in the separatory funnel was then transferred to a beaker with isopropyl alcohol (57 g), thereby producing an alcohol solution of the amino nitrile isomers. This solution was stirred, cooled to approximately 10° C., and maintained at that temperature for about ½ to 1 hr. so as to crystallize the product 2,2-diphenyl-4-(dimethylamino)-pentane nitrile. The crystalline product was recovered by filtration, washed with two aliquots of cold (less than 10° C.) isopropyl alcohol (20 ml each), dried and weighed. Yield was 32.3 g (45%) of the product which exhibited a melting point of 89°-90° C. As a basis of comparison, the melting point of the methadone precursor produced by the conventional commercial process was measured at 90.2°-91.0. The melting point of a mixture of equal weights of the commercial material and the material of this example was 89.5°-90.2° C.

EXAMPLE 2

Several reactions between diphenylacetonitrile, 1-(dimethylamino)-2-chloropropane and base were carried out to compare the results achieved with no catalyst vs. the results achieved in the presence of various quaternary ammonium and phosphonium salts.

In the first run of this example, a 350 ml, round bottom, 3-neck flask equipped with a mechanical stirrer, nitrogen flow, a thermometer, and a condenser was charged with diphenylacetonitrile (25 g, 0.13 moles) 1-dimethylamino-2-chloropropane hydrochloride (25 g), 50% aqueous sodium hydroxide solution (40 g), water (20 ml), and toluene (65 ml). No catalyst was charged. The charge mixture was stirred under nitrogen, heated to reflux and held at reflux for 2 hr. Heating was then terminated, and the reaction mixture was cooled to less than 80° C. and transferred to a separatory funnel using 100 ml of water.

In the separatory funnel the phases were allowed to separate and the water phase was drawn off the bottom and discarded. The toluene phase (91 ml, 84 g) was submitted for amino nitrile assay. The product was not recovered.

In the remaining reaction runs of this example, the charge was the same as in the initial run except that a quaternary ammonium or phosphonium salt catalyst was also included in the charge mixture. Reaction and separation were carried out in the same manner as for the first run.

Table I sets forth, for each of the runs of this example, the catalyst used, the amount of catalyst, the volume and weight of the washed toluene phase recovered after the separation of the water phase and the relative proportions of diphenylacetonitrile and amino nitriles in the toluene phase after washing.

TABLE I

| Run No. | Catalyst type | amount | Toluene Phase Wt. | Vol. | diphenyl-acetonitrile w/w% | aminonitrile w/w% |
|---|---|---|---|---|---|---|
| 1 | none | — | 84 g | 91 ml | 22.4 | 77.6 |

TABLE I-continued

| Run No. | Catalyst type | amount | Toluene Phase Wt. | Vol. | diphenyl-acetonitrile w/w% | aminonitrile w/w% |
| --- | --- | --- | --- | --- | --- | --- |
| 2 | tetrabutyl-ammonium chloride | 3.6g | 88 | 96 | 1.5 | 98.5 |
| 3 | tetrabutyl-ammonium bromide | 4.2 | 88 | 95 | 0.1 | 99.3 |
| 4 | benzyltriethyl-ammonium chloride | 3.0 | 90 | 95.5 | 18.4 | 81.6 |
| 5 | benzyltriethyl-ammonium bromide | 3.5 | 95.5 | 88 | 16.4 | 83.6 |
| 6 | phenyltrimethyl-ammonium bromide | 2.8 | 93 | 86 | 25.5 | 74.5 |
| 7 | cetyltrimethyl-ammonium bromide | 4.7 | 92 | 86 | 10.0 | 90.0 |
| 8 | Benzyltriphenyl-phosphonium chloride | 5.0 | 93 | 100 | 12.5 | 87.5 |
| 9 | (n-Butyl)-triphenyl-phosphonium bromide | 5.2 | 90 | 98 | 17.9 | 82.1 |

EXAMPLE 3

To a reaction flask of the type described in example 2, were charged diphenylacetonitrile (50 g) 1-dimethylamino-2-chloropropane hydrochloride (50 g) 50% sodium hydroxide solution (80 g), water (40 ml), toluene (125 ml) and tetrabutylammonium bromide (4.2 g). The charge mixture was stirred for 5 min. and then sampled for analysis. Stirring was resumed and the charge mixture heated to reflux with a sample being taken when the mixture had been heated to 75° C. Stirring was continued at reflux with periodic samples being taken from the reaction mixture to determine the extent of conversion at various periods thoughout the reaction cycle. These samples were analyzed to provide a profile for the reaction.

To provide a comparative profile, another reaction was run with the same amounts of the same components of the charge mixture, except for the tetrabutylammonium bromide catalyst which was omitted in the second run. Samples were taken during the reaction cycle and analyzed to provide the data for a reaction profile for the case of no catalyst.

The reaction profiles obtained from the runs of this example are shown in the single FIGURE of the drawing. As this drawing demonstrates, where the quaternary ammonium salt catalyst is used the reaction is substantially complete after two hours whereas a considerably longer reaction period is required to achieve the maximum extent of reaction where no catalyst is charged.

In view of the above, it will be seen that the several objects of the invention are achieved and other advantageous results attained.

As various changes could be made in the above methods without departing from the scope of the invention, it is intended that all matter contained in the above description or shown in the accompanying drawing shall be interpreted as illustrative and not in a limiting sense.

What is claimed is:

1. A process for the preparation of 2,2-diphenyl-4-(dimethylamino)-pentane nitrile comprising the steps of:
preparing a charge mixture comprising diphenylacetonitrile, 1-(dimethylamino)-2-halopropane, a base, water, a water-immiscible organic solvent, and a quaternary salt selected from the group consisting of tetrabutylammonium halides, tetrabutylammonium hydrogen sulfate, cetyltrimethyl ammonium halides, methyltrialkyl ($C_8$–$C_{10}$) ammonium halides and benzyltriphenylphosphonium halides; and
heating said mixture under an inert atmosphere to effect formation of 2,2-diphenyl-4-(dimethylamino)-pentane nitrile by reaction of diphenylacetonitrile, 1-(dimethylamino)-2-halopropane and base.

2. A process as set forth in claim 1 wherein said quaternary salt comprises a tetrabutylammonium salt.

3. A process as set forth in claim 1 wherein said solvent is selected from the group consisting of toluene and xylene.

4. A process as set forth in claim 1 wherein the reaction is carried out substantially at a temperature of at least about 80° C.

5. A process as set forth in claim 1 wherein the concentration of said quaternary salt in the charge mixture is at least about 7% by weight based on the diphenylacetonitrile content thereof.

6. A process as set forth in claim 1 wherein said base is selected from the group consisting of sodium hydroxide and potassium hydroxide.

7. A process as set forth in claim 1 wherein the 2,2-diphenyl-4-(dimethylamino)-pentane nitrile reaction product is recovered from the reaction mixture by further steps comprising;
separating the aqueous phase comprising water by-product of the reaction from the organic phase containing said reaction product;
washing the organic phase by contacting it with water for removal therefrom of said quaternary salt and of reaction by-product salt;
separating the washed organic phase from the wash water;
heating the washed organic phase under vacuum so as to strip off said solvent leaving an oil comprising 2,2-diphenyl-4-(dimethylamino)-pentane nitrile and 2,2-diphenyl-3-methyl-4-(dimethylamino)-butyronitrile;
dissolving said oil in an alcohol; and
cooling the alcohol solution so as to crystallize therefrom 2,2-diphenyl-4-(dimethylamino)-pentane nitrile.

8. A process as set forth in claim 7 wherein said 2,2-diphenyl-4-(dimethylamino)-pentane nitrile is reacted with an ethylmagnesium halide to produce methadone.

* * * * *